(12) United States Patent
Lloyd

(10) Patent No.: US 12,740,755 B2
(45) Date of Patent: Sep. 22, 2026

(54) DIGITAL AUSCULTATION DEVICE

(71) Applicant: Rebekah Lloyd, Laughlintown, PA (US)

(72) Inventor: Rebekah Lloyd, Laughlintown, PA (US)

( * ) Notice: Subject to any disclaimer, the term of this patent is extended or adjusted under 35 U.S.C. 154(b) by 203 days.

(21) Appl. No.: 18/620,877

(22) Filed: Mar. 28, 2024

(65) Prior Publication Data

US 2025/0302423 A1 Oct. 2, 2025

(51) Int. Cl.

| | |
|---|---|
| ***A61B 7/04*** | (2006.01) |
| ***A61B 7/02*** | (2006.01) |
| ***G06F 3/16*** | (2006.01) |
| ***G16H 10/60*** | (2018.01) |
| ***H04R 1/10*** | (2026.01) |
| ***H04R 1/46*** | (2006.01) |
| ***H04R 3/00*** | (2006.01) |

(52) U.S. Cl.

CPC ................ *A61B 7/04* (2013.01); *A61B 7/026* (2013.01); *G06F 3/165* (2013.01); *G16H 10/60* (2018.01); *H04R 1/1041* (2013.01); *H04R 1/46* (2013.01); *H04R 3/005* (2013.01); *H04R 2420/07* (2013.01); *H04R 2430/01* (2013.01)

(58) Field of Classification Search

CPC ........ G16H 10/60; G16H 20/30; G16H 40/67; A61B 5/0022; A61B 5/0059; A61B 5/0006; A61B 5/0024; A61B 5/0205; A61B 5/0002; A61B 5/002; A61B 5/02055; A61B 5/0053; A61B 5/0015; A61B 7/04; A61B 7/026; A61B 7/003; A61N 1/3993; G06F 3/165; G06F 3/16; H04R 1/1041; H04R 1/46; H04R 3/005; H04R 2420/07; H04R 2430/01

See application file for complete search history.

(56) References Cited

U.S. PATENT DOCUMENTS

| | | | | |
|---|---|---|---|---|
| 4,618,986 A | 10/1986 | Hower | | |
| 5,557,681 A | 9/1996 | Thomasson | | |
| 5,604,811 A | 2/1997 | McIntyre | | |
| 9,265,478 B2 | 2/2016 | Wang | | |
| 2013/0231577 A1 * | 9/2013 | Leiderman | A61B 7/04 | 600/485 |

(Continued)

FOREIGN PATENT DOCUMENTS

| | | |
|---|---|---|
| WO | WO2014007857 | 1/2014 |

*Primary Examiner* — Leshui Zhang

(57) ABSTRACT

A digital auscultation device for detecting internal body sounds of a patient includes a personal computing device that can access and modify an electronic health record of a patient. A plurality of recording devices is positionable on the patient to record sounds within a body of the patient. Each recording device has a processor that is electrically coupled to a power source and a transceiver. The transceiver is in wireless communication with the personal computing device. A plurality of microphones is coupled to the processor. Each microphone is exposed within a front side of the recording device to detect the sounds within the body of the patient. The processor converts the sounds into an audio recording. The transceiver transmits the audio recording to the personal computing device. The personal computing device can play the audio recording and save the audio recording to the electronic health record.

9 Claims, 7 Drawing Sheets

(56) References Cited

U.S. PATENT DOCUMENTS

| | | | | |
|---|---|---|---|---|
| 2014/0126732 | A1* | 5/2014 | West | A61B 7/003 381/67 |
| 2020/0029886 | A1* | 1/2020 | Butera, III | A61B 5/4205 |
| 2021/0345985 | A1* | 11/2021 | Cunningham | A61B 7/04 |
| 2023/0293103 | A1* | 9/2023 | Higuchi | G16H 15/00 600/586 |

* cited by examiner

DIGITAL AUSCULTATION DEVICE

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to stethoscopes and more particularly pertains to a new stethoscope for detecting internal body sounds of a patient.

(2) Description of Related Art Including Information Disclosed Under 37 CFR 1.97 and 1.98

The prior art relates to stethoscopes. Stethoscopes are one of the most common tools that medical personnel use to listen to the internal body sounds of a patient. For example, a stethoscope may be used to examine the sounds of the heart, lungs, or other organs of the patient. For some patients, such as young children, the stethoscope can be frightening, or the patient may have difficulty sitting still and quiet while the physician listens to the internal body sounds with the stethoscope. Thus, there is a need for a device that can be applied by a parent or caregiver to provide access to the internal body sounds of young children. Once the medical personnel listen to the internal body sounds, however, there is no way for another individual to listen to those same sounds to provide a second opinion. Thus, there is a need for an auscultation device that can create recordings of the internal body sounds for subsequent review or comparison.

BRIEF SUMMARY OF THE INVENTION

An embodiment of the disclosure meets the needs presented above by generally comprising a personal computing device that is configured to access and modify an electronic health record of a patient. A plurality of recording devices is configured to be removably positionable on the patient wherein the plurality of recording devices is configured to record sounds within a body of the patient. Each recording device of the plurality of recording devices comprises a front side and an interior space. A power source is positioned in the interior space. A processor is electrically coupled to the power source. A transceiver is electrically coupled to the processor. The transceiver is in wireless communication with the personal computing device. A plurality of microphones is electrically coupled to the processor. Each microphone of the plurality of microphones has a forward face that is exposed within the front side wherein the plurality of microphones is configured to detect the sounds within the body of the patient. The processor is configured to convert the sounds into an audio recording. The transceiver is configured to transmit the audio recording to the personal computing device. The personal computing device is configured to play the audio recording. The personal computing device is further configured to save the audio recording to the electronic health record.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
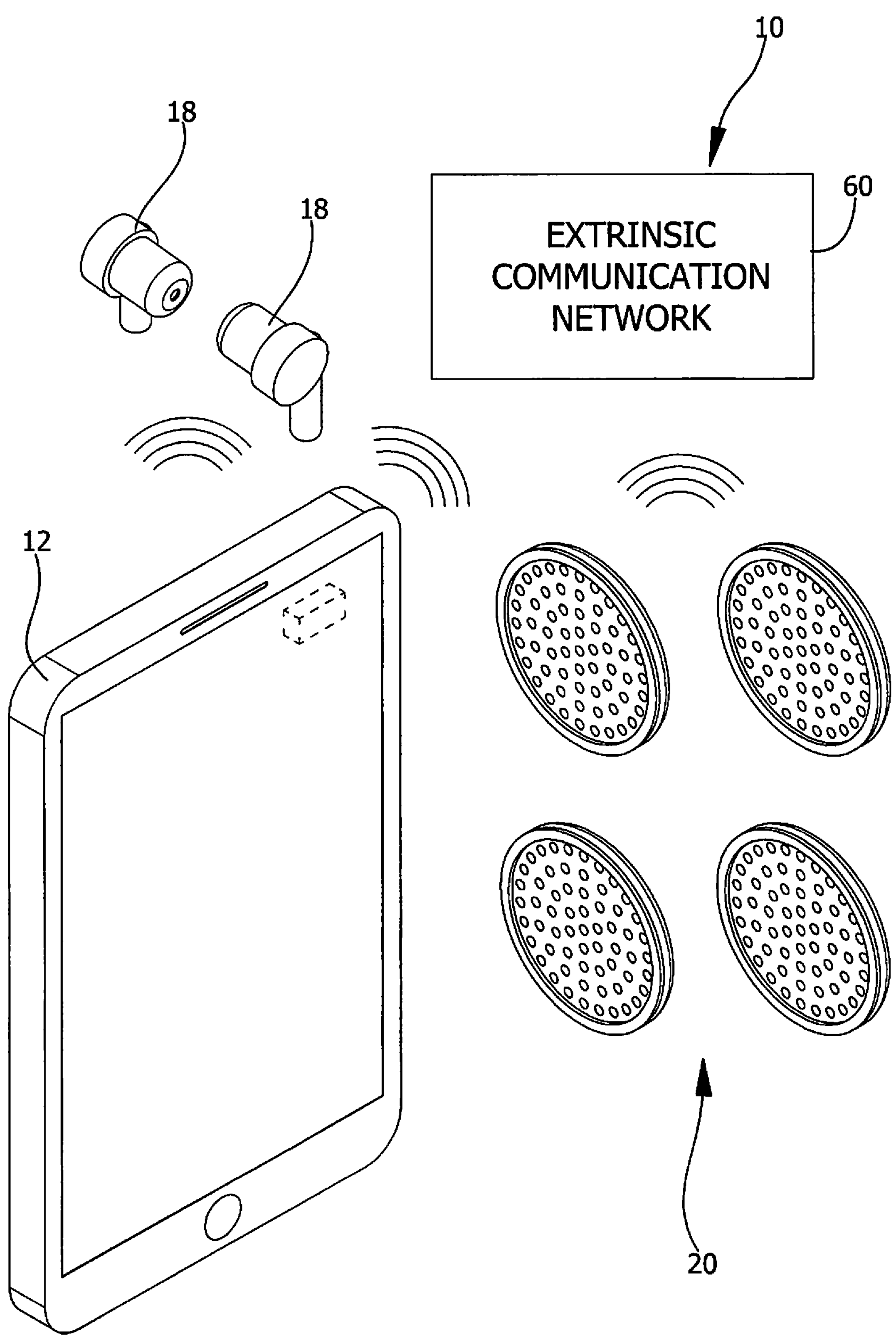
FIG. 1 is an isometric view of a digital auscultation device according to an embodiment of the disclosure.
Figure 2:
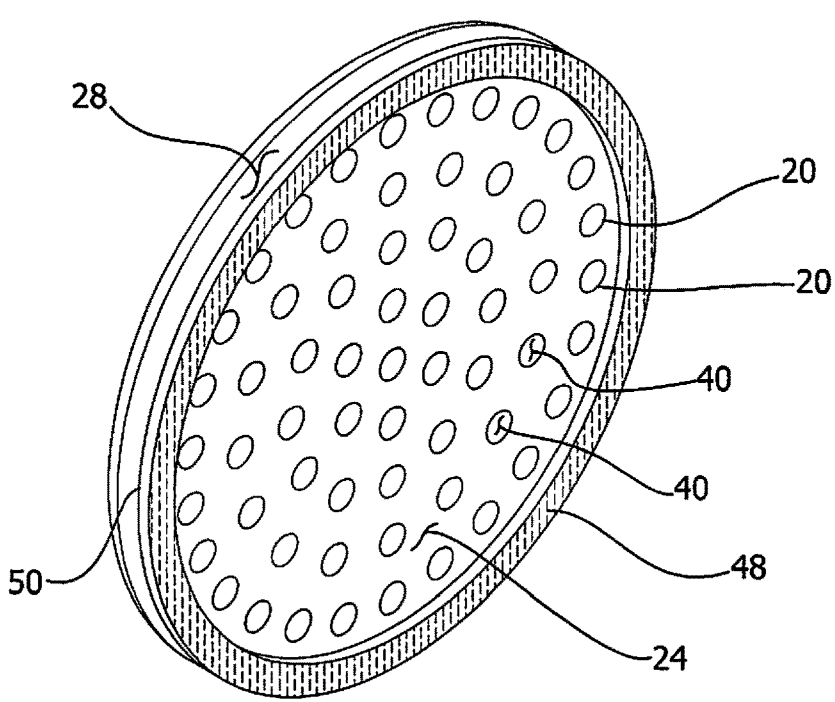
FIG. 2 is a top front isometric view of an embodiment of the disclosure.
Figure 3:
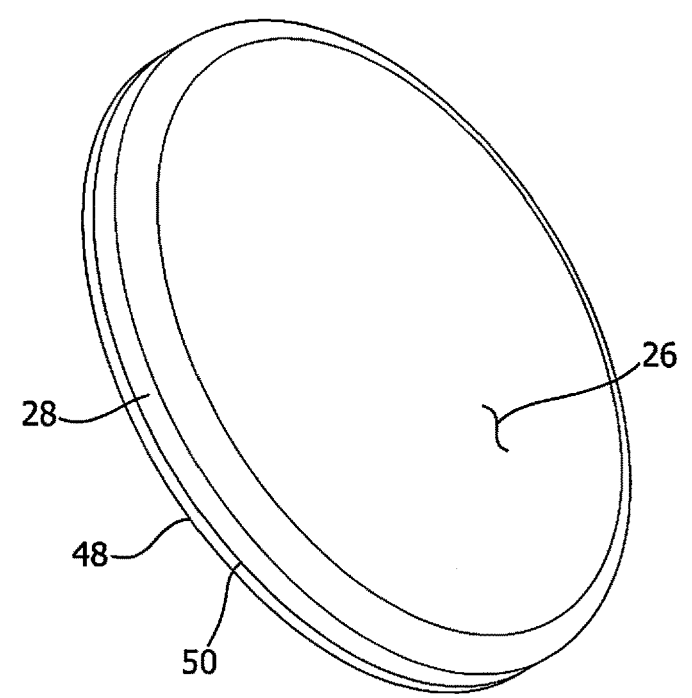
FIG. 3 is a bottom rear isometric view of an embodiment of the disclosure.
Figure 4:
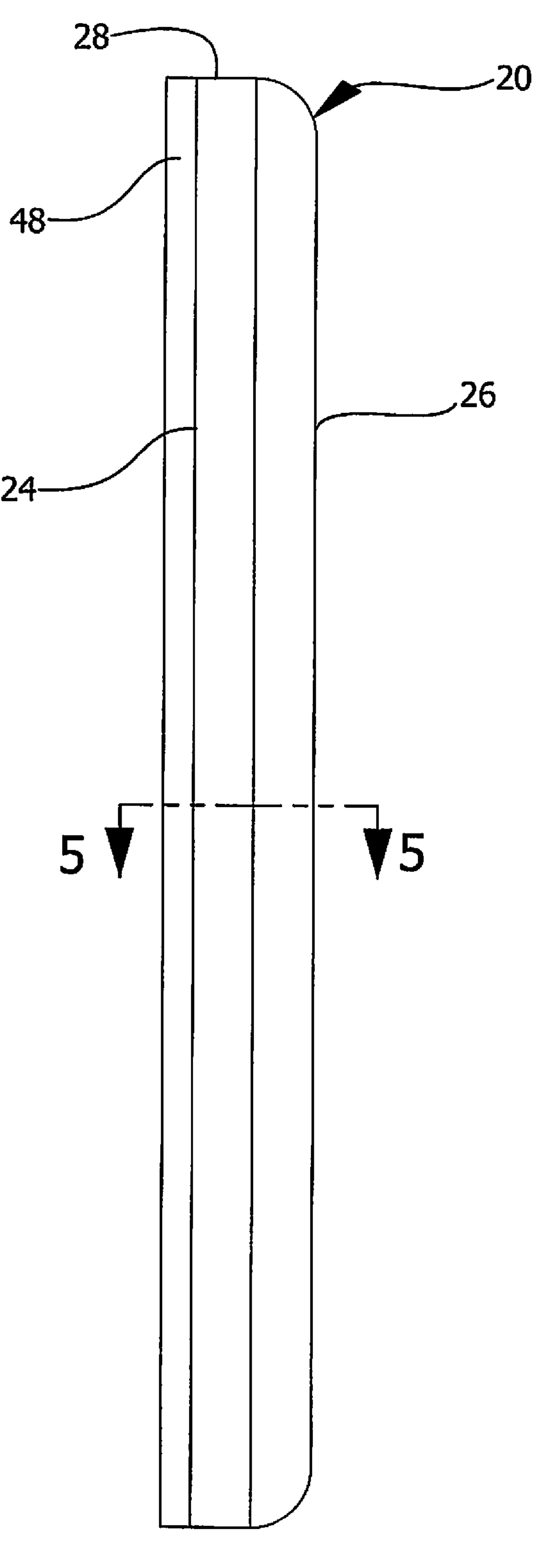
FIG. 4 is a side view of an embodiment of the disclosure.
Figure 5:
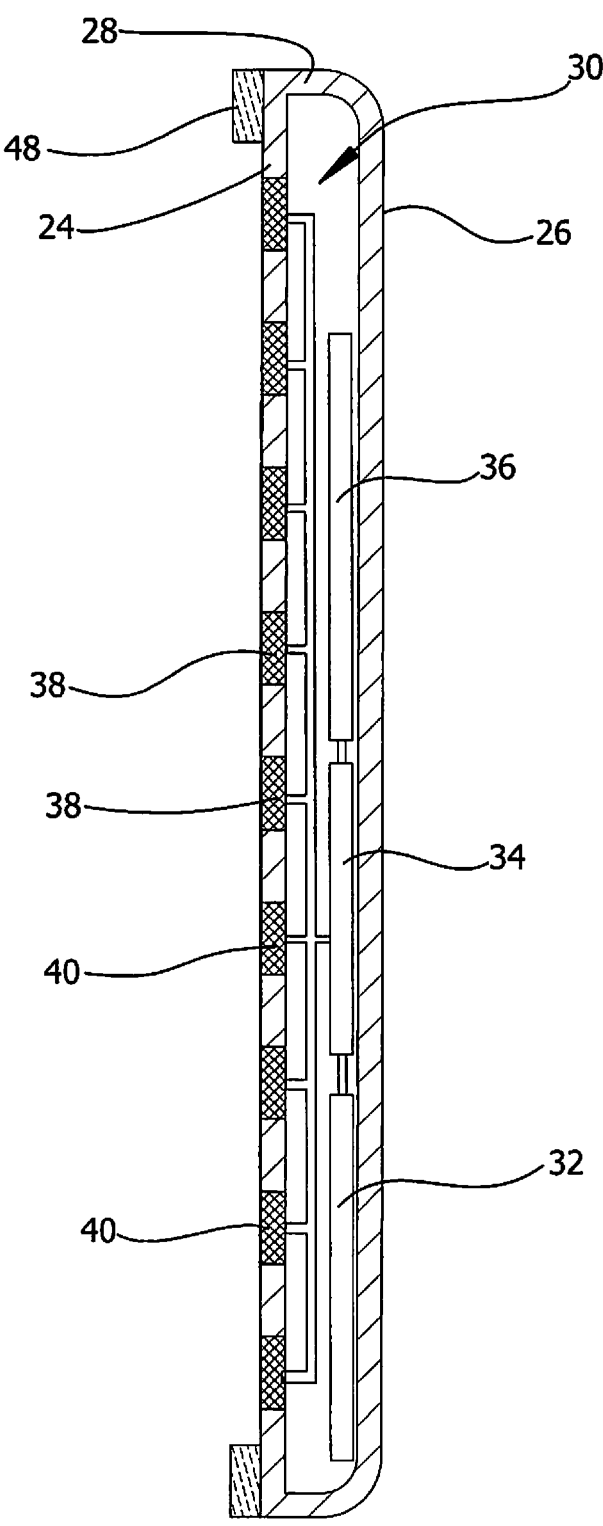
FIG. 5 is a cross-sectional view of an embodiment of the disclosure.
Figure 6:
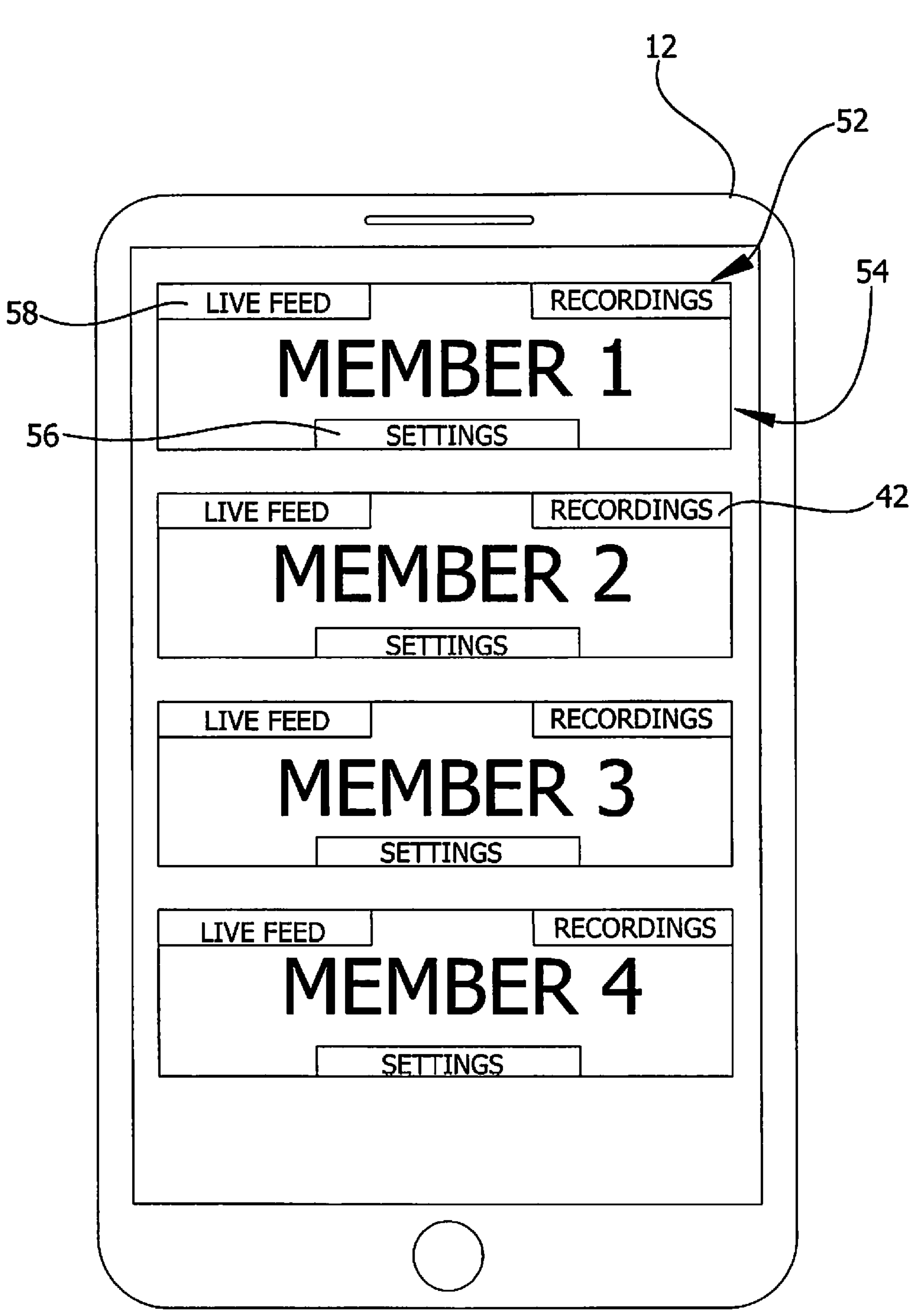
FIG. 6 is a perspective view of an embodiment of the disclosure.
Figure 7:
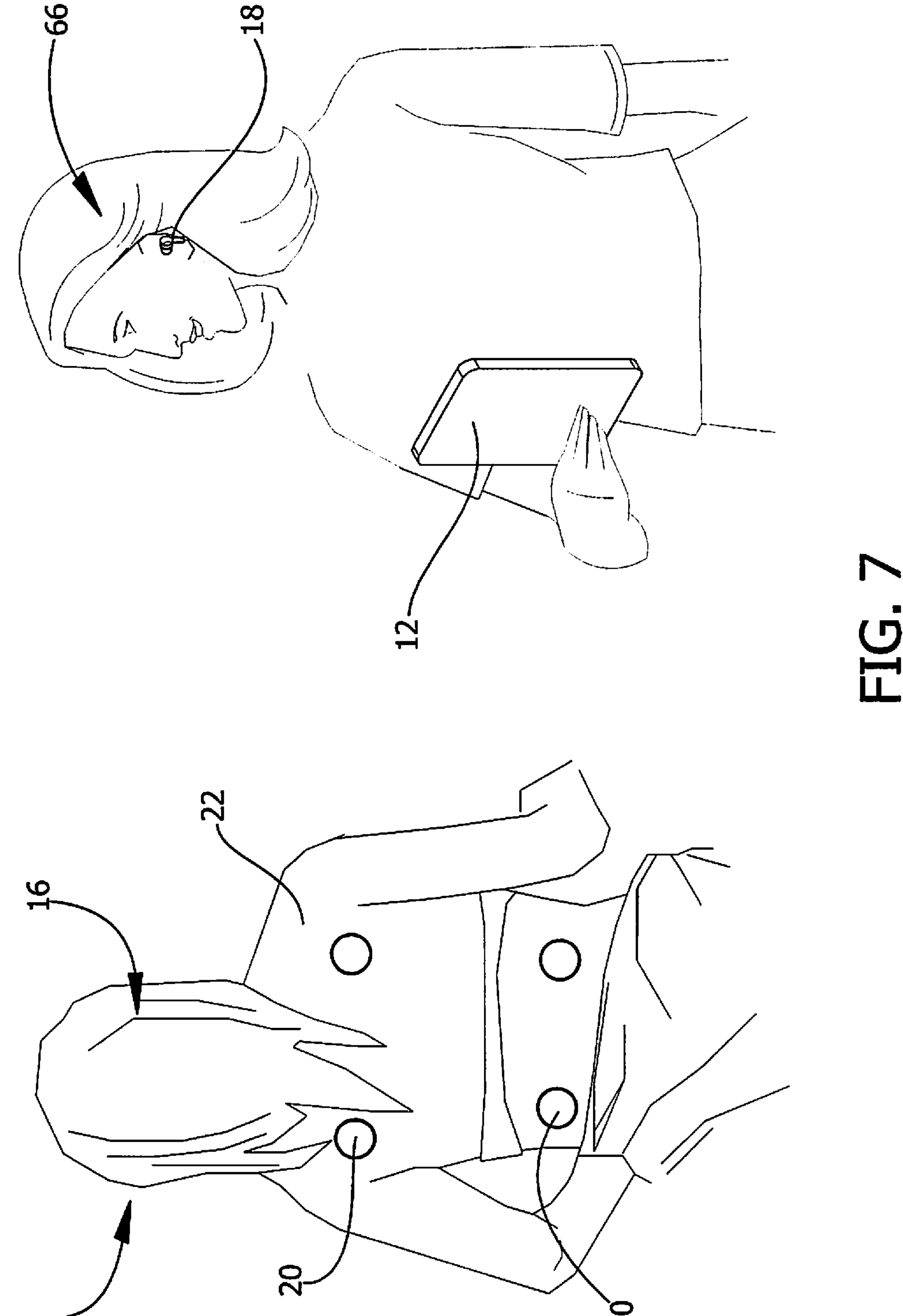
FIG. 7 is an in-use view of an embodiment of the disclosure.
Figure 8:
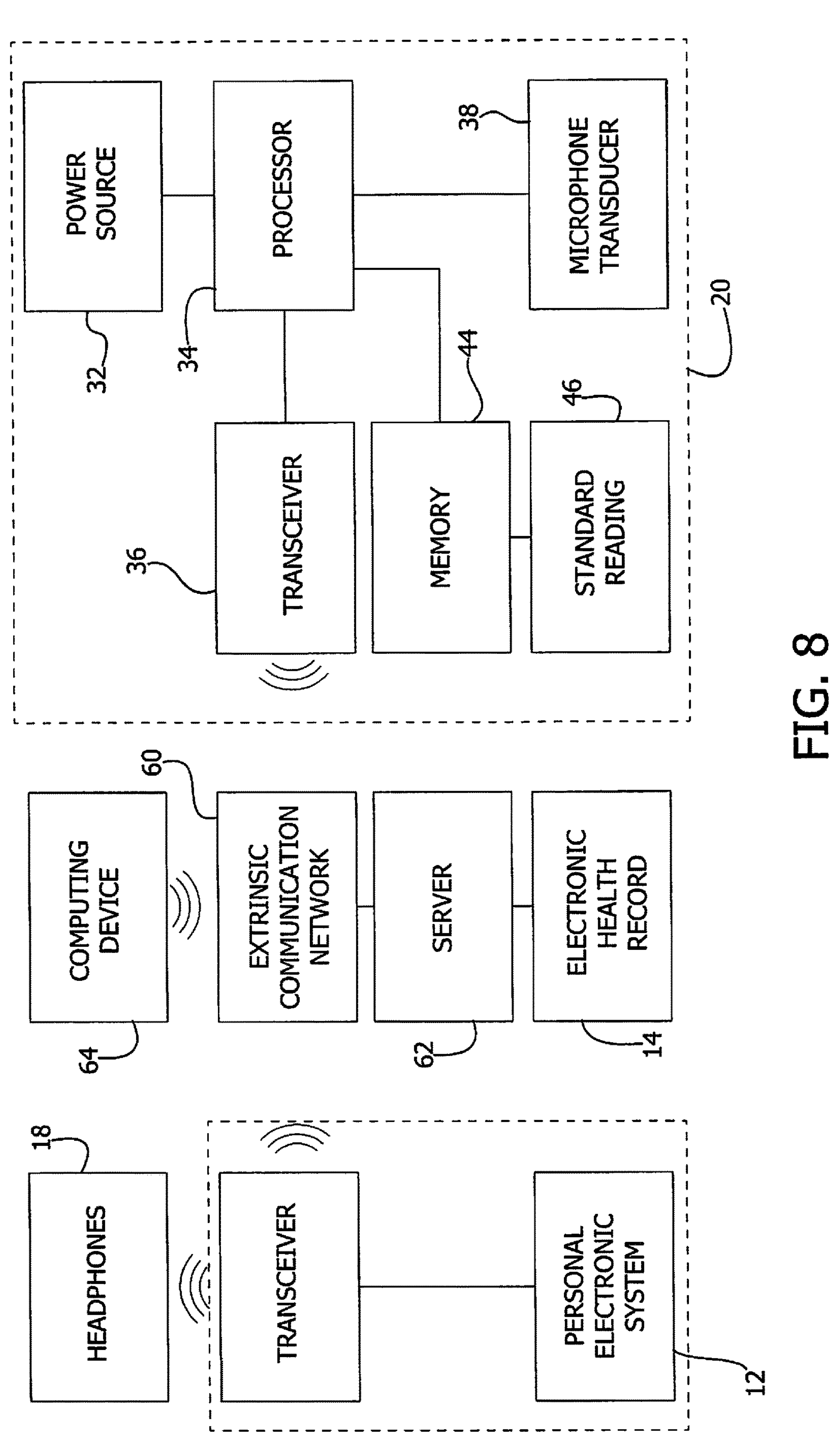
FIG. 8 is a block diagram view of an embodiment of the disclosure.

With reference now to the drawings, and in particular to FIGS. 1 through 8 thereof, a new stethoscope embodying the principles and concepts of an embodiment of the disclosure and generally designated by the reference numeral 10 will be described.

As best illustrated in FIGS. 1 through 8, the digital auscultation device 10 generally comprises a personal computing device 12 is configured to access and modify an electronic health record 14 of a patient 16. For example, the personal computing device 12 may including one or more of a cellular phone, a tablet, a laptop, or a desktop computer. A pair of wireless headphones 18 may be in wireless communication with the personal computing device 12.

A plurality of recording devices 20 is configured to be removably positionable on the patient 16. The plurality of recording devices 20 is configured to amplify and record sounds within a body 22 of the patient 16. For example, the plurality of recording devices 20 can enable a user 66, such as a physician, to hear sounds from the heart or lungs of the patient 16. The plurality of recording devices 20 may include one or more recording devices, as needed to amplify and record the sounds within the body 22 of the patient 16. For example, the plurality of recording devices 20 may include a single recording device. In the example shown in FIG. 7, the plurality of recording devices 20 includes four recording devices. Hearing sounds within different areas of the body 22 may require use of different numbers of recording devices. Additionally, different patients may require a different number of the plurality of recording devices 20. For example, an infant patient may only require a single recording device to hear sounds within the heart or lungs, but an adult patient may require multiple recording devices to hear sounds within the same area of the body 22.

Each recording device of the plurality of recording devices 20 may include a front side 24, a back side 26, and a peripheral side 28 that is coupled to and extends between the front side 24 and the back side 26 to define an interior space 30. A power source 32 is positioned in the interior space 30. For example, the power source 32 may comprise a battery. A processor 34 is electrically coupled to the power source 32. The processor 34 is generally positioned in the interior space 30. A transceiver 36 is electrically coupled to the processor 34. The transceiver 36 is in wireless communication with the personal computing device 12. The transceiver 36 is generally positioned in the interior space 30.

A plurality of microphones 38 is electrically coupled to the processor 34. The plurality of microphones 38 may be inset to the front side 24 and the plurality of microphones 38 may be exposed within the front side 24. For example, each microphone of the plurality of microphones 38 may have a forward face 40 that is exposed within the front side 24 wherein the plurality of microphones 38 are configured to detect the sounds within the body 22 of the patient 16. The forward face 40 of each microphone of the plurality of microphones 38 is generally coplanar with the front side 24.

The processor 34 is configured to convert the sounds into an audio recording 42. The transceiver 36 is configured to transmit the audio recording 42 to the personal computing device 12. The personal computing device 12 is configured to play the audio recording 42 through the pair of wireless headphones 18, or through a speaker of the personal computing device 12. The personal computing device 12 is further configured to save the audio recording 42 to the electronic health record 14.

The processor 34 may have a memory 44 that is configured to store a standard reading 46 of the sounds within the body 22 of the patient 16. The processor 34 is configured to compare the sounds to the standard reading 46. The transceiver 36 is configured to send an alert to the personal computing device 12 when the sounds deviate from the standard reading 46. For example, the memory 44 may include a standard reading 46 for a heart rate or rhythm for the patient 16. When the processor 34 recognizes that the sounds detected by one or more of the plurality of microphones 38 deviate from the standard reading 46 for the heart rate or rhythm of the patient 16, the transceiver 36 will send an alert to the personal computing device 12 to notify the user 66 that the patient 16 may be in cardiac distress. In another example, the memory 44 may include a standard reading 46 for a decibel level for sounds originating in the lungs of the patient 16. When the processor 34 recognizes that the sounds detected by one or more of the plurality of microphones 38 deviate from the standard reading 46, the transceiver 36 will send an alert to the personal computing device 12 to notify the user 66 that the patient 16 may be in respiratory distress.

An adhesive pad 48 may be coupled to the front side 24 of each recording device of the plurality of recording devices 20. The adhesive pad 48 is configured to removably couple each recording device of the plurality of recording devices 20 to the patient 16. The adhesive pad 48 may extend around an outer edge 50 of the front side 24 wherein the adhesive pad 48 surrounds the plurality of microphones 38 of each recording device of the plurality of recording devices 20.

The personal computing device 12 may have an application 52 that is configured to provide a user interface 54 between the personal computing device 12 and the plurality of recording devices 20. For example, the user interface 54 may facilitate the user 66 in accessing the audio recording 42 from each recording device of the plurality of recording devices 20. The application 52 may be configured to enable the user 66 to adjust a plurality of audio settings 56 of each recording device of the plurality of recording devices 20. For example, the plurality of audio settings 56 may include an amplification factor and a playback volume. The application 52 may be further configured to enable the user 66 to access a real-time audio feed 58 of the sounds within the body 22 of the patient 16 from each recording device of the plurality of recording devices 20.

An extrinsic communication network 60 may be wirelessly connected to the personal computing device 12. The extrinsic communication network 60 may also be in wireless communication with the transceiver 36. For example, the extrinsic communication network 60 may be a wireless personal access network such as a BLUETOOTH® network, or a computer network.

The extrinsic communication network 60 may include a server 62 that is configured to store the electronic health record 14. The extrinsic communication network 60 may also include a secondary computing device 64 that is configured to access and modify the electronic health record 14 of the patient 16. The transceiver 36 of each recording device of the plurality of recording devices 20 may be configured to send the alert to the secondary computing device 64 when the sounds deviate from the standard reading 46. For example, the secondary computing device 64 may belong to a member of the patient's medical team, such as a doctor, a nurse, or a parent of the patient 16. The transceiver 36 may thus alert two individuals, such as a primary care physician and a specialist, or such as a parent and a doctor, that the patient 16 may be in distress. Through the extrinsic communication network 60, multiple members of the patient's medical team can access the audio recording 42, or the real-time audio feed 58, of the sounds within the body 22 of the patient 16.

In use, the plurality of recording devices 20 can be positioned on the body 22 of the patient 16, over an area where the user 66 wants to hear sounds within the body 22 of the patient 16. For example, if the patient 16 is pregnant, the plurality of recording devices 20 may be positioned on the abdomen of the patient 16. In another example, such as the one shown in FIG. 7, the plurality of recording devices

20 may be positioned on the back of the user 66 to hear sounds from the lungs. Because the adhesive pad 48 makes the plurality of recording devices 20 easy to position on the patient 16, a parent or caregiver can position the plurality of recording devices 20 on the patient 16. For example, when the patient 16 is a young child, having the trusted caregiver place the plurality of recording devices 20 on the body 22 of the patient 16 may make the patient 16 feel more comfortable and less anxious.

The user 66 may access one recording device of the plurality of recording devices 20 on the application 52 to listen to the real-time audio feed 58 of the sounds within the body 22 of the patient 16 where that recording device is placed. Alternatively, the user 66 may access the audio recording 42 of the sounds captured by the plurality of microphones 38 within each recording device of the plurality of recording devices 20. When the sounds deviate from the standard reading 46 that is expected at the places where the plurality of recording devices 20 are positioned, the transceiver 36 will send the alert to the user 66 to alert the user 66 that the patient 16 may be in distress. Because the transceiver 36 in each recording device of the plurality of recording devices 20 may be in wireless communication with an extrinsic communication network 60, multiple user 66*s* may access the real-time audio feed 58 and the audio recording 42 of the sounds captured by the plurality of recording devices 20. For example, both members of the medical team and family members of the patient 16 may have access to the audio recording 42. Additionally, both the medical team and the family members may receive the alert that the patient 16 may be in distress, increasing the probability that someone will be able to respond and check on the patient 16.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. An auscultation system comprising:

a personal computing device being configured to access and modify an electronic health record of a patient;

a plurality of recording devices being configured to be removably positionable on the patient wherein the plurality of recording devices is configured to record sounds within a body of the patient, each recording device of the plurality of recording devices comprising:

a front side and an interior space;

a power source being positioned in the interior space;

a processor being electrically coupled to the power source;

a transceiver being electrically coupled to the processor, the transceiver being in wireless communication with the personal computing device;

a plurality of microphones being electrically coupled to the processor, each microphone of the plurality of microphones having a forward face being exposed within the front side wherein the plurality of microphones is configured to detect the sounds within the body of the patient;

the processor being configured to convert the sounds into an audio recording;

the transceiver being configured to transmit the audio recording to the personal computing device, the personal computing device being configured to play the audio recording, the personal computing device being configured to save the audio recording to the electronic health record; and an adhesive pad being coupled to the front side of each recording device of the plurality of recording devices wherein the adhesive pad is configured to removably couple each recording device of the plurality of recording devices to the patient, wherein the adhesive pad has a constant width extending around an outer edge of the front side and a constant thickness extending from the front side wherein the adhesive pad surrounds the plurality of microphones of each recording device of the plurality of recording devices.

2. The auscultation system of claim 1, wherein the plurality of microphones is inset to the front side of each recording device of the plurality of recording devices, the plurality of microphones being exposed within the front side of each recording device of the plurality of recording devices.

3. The auscultation system of claim 1, further comprising a pair of wireless headphones being in wireless communication with the personal computing device, the personal computing device being configured to play the audio recording through the pair of wireless headphones.

4. The auscultation system of claim 1, the processor further comprising a memory being configured to store a standard reading, the processor being configured to compare the sounds to the standard reading, the transceiver being configured to send an alert to the personal computing device when the sounds deviate from the standard reading.

5. The auscultation system of claim 4, further comprising an extrinsic communication network being wirelessly connected to the personal computing device, the extrinsic communication network being in wireless communication with the transceiver, the extrinsic communication network including a secondary computing device being configured to access and modify the electronic health record of the patient, the transceiver being configured to send the alert to the secondary computing device when the sounds deviate from the standard reading.

6. The auscultation system of claim 1, the personal computing device further comprising an application being configured to provide a user interface between the personal computing device and the plurality of recording devices, the application being configured to enable a user to adjust a plurality of audio settings of each recording device of the plurality of recording devices.

7. The auscultation system of claim 6, the plurality of audio settings further comprising an amplification factor and a playback volume.

8. The auscultation system of claim 6, the application being configured to enable the user to access a real-time audio feed of the sounds within the body of the patient from each recording device of the plurality of recording devices.

9. An auscultation system comprising:

a personal computing device being configured to access and modify an electronic health record of a patient;

a pair of wireless headphones being in wireless communication with the personal computing device;

a plurality of recording devices being configured to be removably positionable on the patient wherein the plurality of recording devices is configured to amplify and record sounds within a body of the patient, each recording device of the plurality of recording devices comprising:

a front side, a back side, and a peripheral side being coupled to and extending between the front side and the back side to define an interior space;

a power source being positioned in the interior space, the power source comprising a battery;

a processor being electrically coupled to the power source, the processor being positioned in the interior space;

a transceiver being electrically coupled to the processor, the transceiver being in wireless communication with the personal computing device, the transceiver being positioned in the interior space;

a plurality of microphones being electrically coupled to the processor, the plurality of microphones being inset to the front side, the plurality of microphones being exposed within the front side, each microphone of the plurality of microphones having a forward face being exposed within the front side wherein the plurality of microphones is configured to detect the sounds within the body of the patient, the forward face of each microphone of the plurality of microphones being coplanar with the front side;

the processor being configured to convert the sounds into an audio recording;

the transceiver being configured to transmit the audio recording to the personal computing device, the personal computing device being configured to play the audio recording through the pair of wireless headphones, the personal computing device being configured to save the audio recording to the electronic health record;

the processor having a memory being configured to store a standard reading, the processor being configured to compare the sounds to the standard reading, the transceiver being configured to send an alert to the personal computing device when the sounds deviate from the standard reading;

an adhesive pad being coupled to the front side of each recording device of the plurality of recording devices wherein the adhesive pad is configured to removably couple each recording device of the plurality of recording devices to the patient, wherein the adhesive pad has a constant width extending around an outer edge of the front side and a constant thickness extending from the front side wherein the adhesive pad surrounds the plurality of microphones of each recording device of the plurality of recording devices;

the personal computing device having an application being configured to provide a user interface between the personal computing device and the plurality of recording devices, the application being configured to enable a user to adjust a plurality of audio settings of each recording device of the plurality of recording devices, the plurality of audio settings including an amplification factor and a playback volume, the application being configured to enable the user to access a real-time audio feed of the sounds within the body of the patient from each recording device of the plurality of recording devices; and an extrinsic communication network being wirelessly connected to the personal computing device, the extrinsic communication network being in wireless communication with the transceiver, the extrinsic communication network including:

a secondary computing device being configured to access and modify the electronic health record of the patient, the transceiver being configured to send the alert to the secondary computing device when the sounds deviate from the standard reading.

* * * * *